(12) United States Patent
Bao et al.

(10) Patent No.: US 8,556,928 B2
(45) Date of Patent: Oct. 15, 2013

(54) STYPTIC DEVICE

(75) Inventors: Bui Bao, Sherbrooke (CA); Richard Gendron, Beaconsfield (CA); Olivier Bertrand, Quebec (CA)

(73) Assignee: Benrikal Services Inc., Beaconsfield (CA)

( * ) Notice: Subject to any disclaimer, the term of this patent is extended or adjusted under 35 U.S.C. 154(b) by 92 days.

(21) Appl. No.: 12/998,928

(22) PCT Filed: Dec. 17, 2009

(86) PCT No.: PCT/CA2009/001827
§ 371 (c)(1),
(2), (4) Date: Aug. 12, 2011

(87) PCT Pub. No.: WO2010/069053
PCT Pub. Date: Jun. 24, 2010

(65) Prior Publication Data
US 2011/0295310 A1    Dec. 1, 2011

Related U.S. Application Data

(60) Provisional application No. 61/193,697, filed on Dec. 17, 2008.

(51) Int. Cl.
*A61M 29/00*    (2006.01)
(52) U.S. Cl.
USPC .......................... 606/203; 128/116.1; 606/157
(58) Field of Classification Search
USPC ......... 606/201–204, 213, 215, 157, 158, 151, 606/111, 112; 602/53, 20, 26; 601/120, 601/134–138, 143, 147, 6, 11; 604/107; 600/495, 499; 128/100.1, 106.1, 112.1, 128/116.1, 118.1, 107.1, 108.1, 109.1, 128/110.1, 111.1, 117.1, 119.1, 120.1, 128/121.1, 124.1, 125.1
See application file for complete search history.

(56) References Cited

U.S. PATENT DOCUMENTS

| | | | |
|---|---|---|---|
| 1,915,623 A * | 6/1933 | Seeley | 128/116.1 |
| 3,586,001 A | 6/1971 | Sanderson | |
| 4,182,338 A | 1/1980 | Stanulis | |
| D274,557 S | 7/1984 | Griffith, III et al. | |

(Continued)

FOREIGN PATENT DOCUMENTS

| CN | 201098167 | 8/2008 |
|---|---|---|
| EP | 614652 A1 | 9/1994 |
| EP | 1358851 | 11/2003 |

*Primary Examiner* — Gary Jackson
*Assistant Examiner* — Katrina Stransky (57) ABSTRACT

A styptic device (10) for substantially hemostatically sealing a percutaneous puncture (12) in a blood vessel (14) of a patient (11), the styptic device (10) comprising: a base (16); a main compression element (18) extending from the base (16), the main compression element (18) defining a main compression surface (24) compressible against the patient (11); and an auxiliary compression element (20) removably attachable to the base (16), the auxiliary compression element (20) defining an auxiliary compression surface (26) compressible against the patient (11). When compressed on the patient (11) substantially in register with the percutaneous puncture (12), the styptic device (10) exerts a first pressure distribution profile on the patient (11) substantially adjacent to the percutaneous puncture (12) when the auxiliary compression element (20) is attached to the base (16) and the styptic device (10) exerts a second pressure distribution profile on the patient (11) substantially adjacent to the percutaneous puncture (12) when the auxiliary compression element (20) is detached from the base (16), the first and second pressure distribution profiles being different from each other.

21 Claims, 4 Drawing Sheets

(56) References Cited

U.S. PATENT DOCUMENTS

| | | |
|---|---|---|
| 4,997,438 A | 3/1991 | Nipper |
| 5,010,902 A | 4/1991 | Rambo et al. |
| 5,078,728 A | 1/1992 | Giarratano |
| 5,269,803 A | 12/1993 | Geary et al. |
| 5,512,056 A | 4/1996 | Stevens et al. |
| 5,583,890 A | 12/1996 | Bromley |
| 5,618,302 A | 4/1997 | Martin |
| D381,427 S | 7/1997 | Marrero |
| 5,643,315 A | 7/1997 | Daneshvar |
| 5,695,520 A | 12/1997 | Bruckner et al. |
| 5,728,120 A | 3/1998 | Shani et al. |
| 6,149,666 A | 11/2000 | Marsden |
| 6,189,538 B1 | 2/2001 | Thorpe |
| 6,752,820 B1 | 6/2004 | Hafemann |
| 6,827,727 B2 | 12/2004 | Stalemark et al. |
| 7,247,163 B2 | 7/2007 | Akerfeldt |
| D548,350 S | 8/2007 | Jordan et al. |
| 2003/0229375 A1 | 12/2003 | Fleischer |
| 2004/0013715 A1 | 1/2004 | Wnek et al. |
| 2004/0098035 A1* | 5/2004 | Wada et al. .......... 606/201 |
| 2004/0243044 A1 | 12/2004 | Penegor et al. |
| 2007/0239092 A1* | 10/2007 | Ross .......... 602/20 |
| 2008/0183207 A1 | 7/2008 | Horne |
| 2009/0005804 A1 | 1/2009 | Esposito et al. |

\* cited by examiner

STYPTIC DEVICE

The present application is a National Stage Entry of PCT Application Serial Number PCT/CA2009/001827 filed on Dec. 17, 2009, which application claims priority from U.S. Provisional Patent Application Ser. No. 61/193,697 filed on Dec. 17, 2008.

FIELD OF THE INVENTION

The present invention relates to the general field of medical devices and is particularly concerned with a styptic device for hemostatically sealing percutaneous vascular punctures.

BACKGROUND

There exists a plurality of medical and/or surgical procedures that are carried out intravascularly or intralumenally. For example, in the treatment of vascular diseases, such as atherosclerosis, percutaneous angioplasty and stenting are now widely accepted procedures.

Such procedures usually involve the percutaneous puncture and insertion of a hollow needle through a patient's skin and muscle tissue into the vascular system. A guide wire is then typically passed through the needle lumen into the patient's blood vessel accessed by the needle. The needle may be removed, and an introducer sheath may be advanced over the guide wire into the vessel, for example, in conjunction with or subsequent to, a dilator.

A catheter or other device may then be advanced through a lumen of the introducer sheath and over the guide wire into position for performing a medical procedure such as, dilating the vessel, stenting of the latter, or the like.

In percutaneous transluminal coronary angioplasty, the catheter is typically introduced either in the radial or femoral artery and advanced through the artery to the coronary region. Catheters typically have a diameter in the range of one millimeter and four millimeters, hence creating a significant puncture in the artery. Also, during the procedure, the catheter may be twisted or otherwise manipulated as it is advanced to the treatment site, hence potentially causing a further enlargement of the puncture.

Upon completion of the procedure, the devices and introducer sheath may be removed, leaving a puncture site in the vessel wall. Such procedures hence unavoidably present the problem of stopping the bleeding at the percutaneous puncture site after the procedure has been completed and after the instrument and any introducer sheaths used therewith have been removed.

At present, such bleeding is sometimes stopped by the application of direct digital pressure over the puncture site by a trained physician or other suitably trained medical personnel. Such direct pressure has to be properly applied for a sufficiently long period of time for hemostasis to occur so that the opening is effectively closed against further bleeding. The application of direct digital pressure over the puncture site, although somewhat useful, nevertheless suffers from numerous drawbacks.

First, the direct digital pressure application procedure constitutes an inefficient, if not wasteful, use of medical professional services. For example, in the case of punctures into relatively high pressure vessels, such as into the femoral artery or superficial femoral arteries, the pressure may have to be applied for as long as forty-five minutes for hemostasis to occur.

Second, the application of digital pressure over a relatively long period of time may result in fatigue, numbness, stiffness and/or pain occurring in the fingers, hands, wrists and/or forearms of the practitioner performing the procedure. Furthermore, repetition of the procedure over a period of time may cause repetitive-type stress injuries, such as carpal tunnel syndrome or the like.

Still furthermore, although the procedure is typically performed with gloves there exists a possibility that the glove could already have, or may develop, a tear, thereby allowing direct pressurized digital contact with potentially contaminating bodily fluids.

Third, it is often difficult for an individual to exert digital pressure of optimal magnitude, especially over a relatively long period of time. The magnitude of the pressure exerted may however prove to be particularly important in some situations. Indeed, should the magnitude of the pressure be suboptimal, a bruise or hematoma may form at the entry site since internal bleeding of the punctured artery continues until clotting blocks the puncture. On the contrary, should the applied pressure be too great, this may result in a substantial reduction, if not virtual arrest, of the flow of blood through the vessel. This, in turn, may lead to thrombosis of the vessel with potentially serious complications.

Yet another drawback associated with the conventional digital application of pressure at the puncture site results from the fact that the instrument and any introducer sheath used therewith is typically completely withdrawn prior to the application of pressure at the puncture site. This results in a brief, yet vigorous, free-flow of blood through the puncture site, which may obscure the exact location of the puncture momentarily leading to further blood loss.

Still furthermore, the conventional method of digital pressure application of the puncture site is sometimes considered uncomfortable for the patient and requires that the patient remain immobilized in the operating room, catheter lab, holding area or the like, hence using up valuable space.

Some styptic devices as been shown in the prior art. However, such prior art devices suffer from numerous drawbacks. Indeed, prior art device generally suffer from being unergonomical to the user and uncomfortable to the patient. Prior art devices also suffer from being overall too complex, and, hence, relatively expensive and potentially unreliable.

Accordingly, there exists a need for an improved styptic device for hemostatically sealing percutaneous vascular punctures. It is a general objective of the present invention to provide such an improved styptic device.

SUMMARY OF THE INVENTION

In a broad aspect, the invention provides a styptic device for substantially hemostatically sealing a percutaneous puncture in a blood vessel of a patient, the styptic device comprising: a base; a main compression element extending from the base, the main compression element defining a main compression surface compressible against the patient; and an auxiliary compression element removably attachable to the base, the auxiliary compression element defining an auxiliary compression surface compressible against the patient. When compressed on the patient substantially in register with the percutaneous puncture, the styptic device exerts a first pressure distribution profile on the patient substantially adjacent to the percutaneous puncture when the auxiliary compression element is attached to the base and said styptic device exerts a second pressure distribution profile on the patient substantially adjacent to the percutaneous puncture when the auxiliary compression element is detached from the base, the first and second pressure distribution profiles being different from each other.

Advantageously, the proposed styptic device is relatively efficient at stopping blood flow through the percutaneous puncture while being substantially comfortable to the patient to which the styptic device is attached. Use of the auxiliary compression component allows for adapting the styptic device to patients having different morphologies, or for the use of the same styptic device at various anatomical locations.

The styptic device is relatively easily manufacturable using known components and methods and is also relatively easily usable using a sequence of quick and ergonomic steps.

In some embodiments of the invention, the styptic device is relatively easily positionable in register with the puncture due to the use of a substantially transparent material in the main compression element.

In another broad aspect, the invention provides a styptic device for substantially hemostatically sealing a percutaneous puncture in a blood vessel of a patient, the styptic device comprising: a base, a main compression element extending from the base, the main compression element defining a main compression surface compressible against the patient; the main compression element having a shape, dimensions and mechanical properties such that the main compression element protrudes in the percutaneous puncture when the main compression surface is compressed against the patient in register with the percutaneous puncture.

In another broad aspect, the invention provides a method for substantially hemostatically sealing a percutaneous puncture in a blood vessel of a subject using a substantially deformable compression element, the method comprising: compressing with a compression pressure the compression element against the subject substantially in register with the percutaneous puncture; and deforming the compression element so that the compression element protrudes in the percutaneous puncture.

In some embodiments of the invention, deformation of the compression element into the puncture helps in reducing the time required before blood flow through the puncture is interrupted and removal of the styptic device from the intended user is allowed.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the drawings:

FIG. 7, in a partial side cross-sectional view taken along the line VII-VII of FIG. 6, illustrates the styptic device shown in FIGS. 1 to 6;

DETAILED DESCRIPTION

Figure 1:
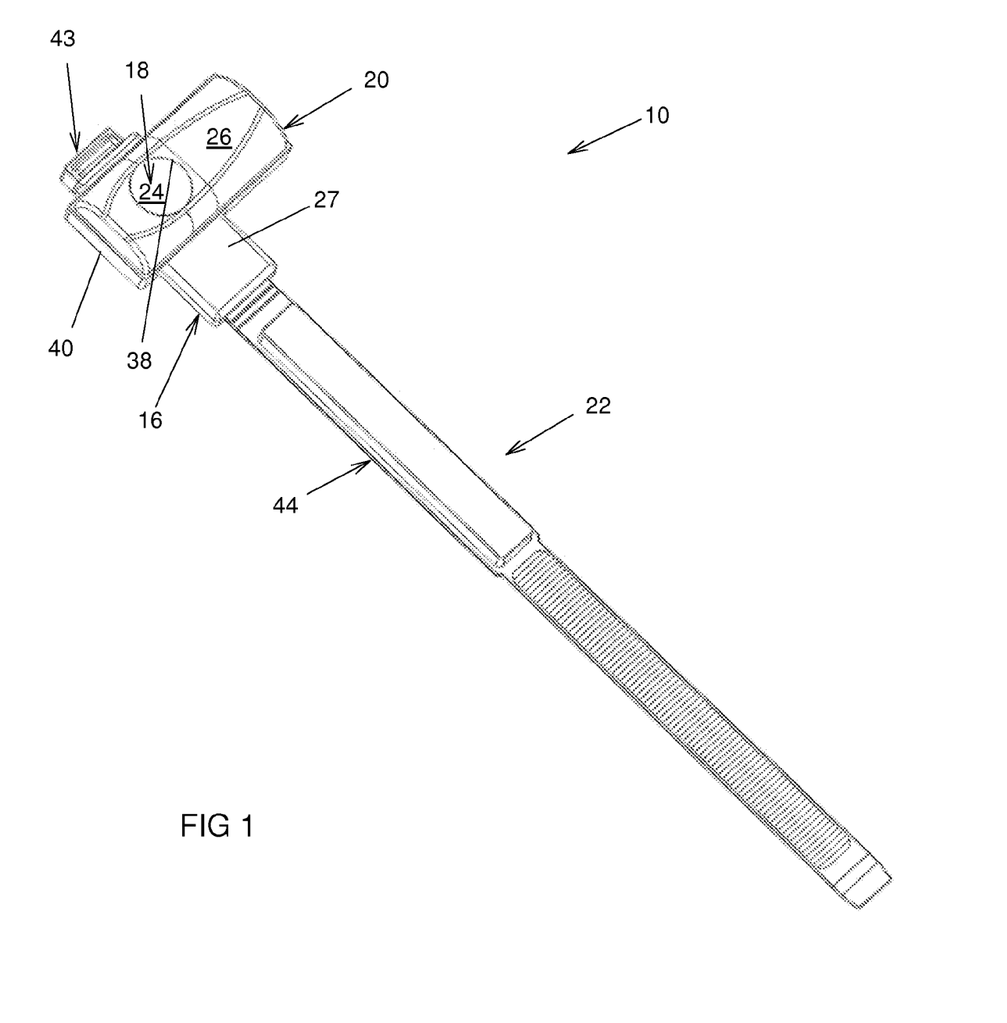
FIG. 1, in a perspective view, illustrates a styptic device in accordance with an embodiment of the present invention, the styptic device being shown with an auxiliary compression element attached.
Figure 9:
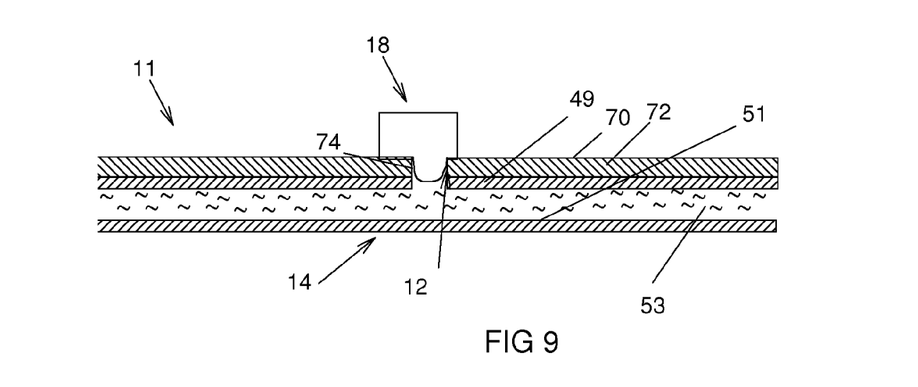
FIG. 9: in a schematic side cross-sectional view, illustrates the percutaneous puncture shown in FIG. 8 compressed with a compression element part of the styptic device shown in FIGS. 1 to 8.

Referring to FIG. 1, there is shown a styptic device 10 in accordance with an embodiment of the present invention. As illustrated schematically in FIG. 9, the styptic device 10 is usable for substantially hemostatically sealing a percutaneous puncture 12 in a blood vessel 14 of a patient 11, only part of which is seen in FIG. 9. Returning to FIG. 1, the styptic device 10 includes a base 16 and a main compression element 18 extending from the base 16. An auxiliary compression element 20 is removably attachable the base 16. In some embodiments of the invention, the styptic device 10 includes an attachment 22 operatively coupled to the base 16 for attaching the styptic device 10 to the patient 11.

The main compression element 18 defines a main compression surface 24 compressible against the patient 11. The auxiliary compression element 20 defines an auxiliary compression surface 26 also compressible against the patient 11. When compressed against the patient 11 substantially in register with the percutaneous puncture 12, the styptic device 10 exerts a first pressure distribution profile on the patient 11 substantially adjacent to the percutaneous puncture 12 when the auxiliary compression element 20 is attached to the base 16 and the styptic device 10 exerts a second pressure distribution profile on the patient 11 substantially adjacent to the percutaneous puncture 12 when the auxiliary compression element 20 is detached from the base 16, the first and second pressure distribution profiles being different from each other. Such pressure distribution profiles are described in further details hereinbelow.

Advantageously, the proposed auxiliary compression element 20 varies the dimensions of and the pressure profile exerted by the styptic device 10, which increases greatly its flexibility in use on patients 11 of different morphology and in use of the styptic device 10 for hemostatically sealing percutaneous punctures 12 at different anatomical location on patients 11.

Figure 5:
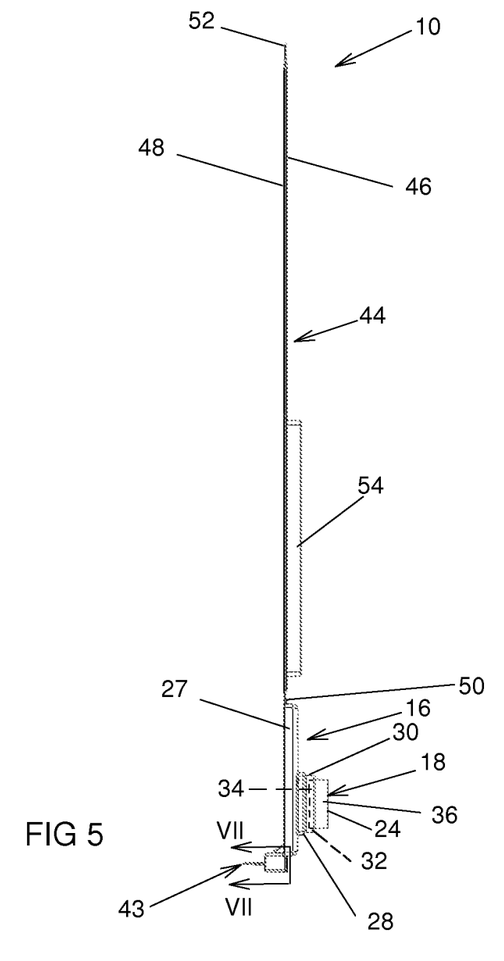
FIG. 5, in a side elevation view, illustrates the styptic device shown in FIGS. 1 to 4 with the auxiliary compression element detached therefrom.
Figure 6:
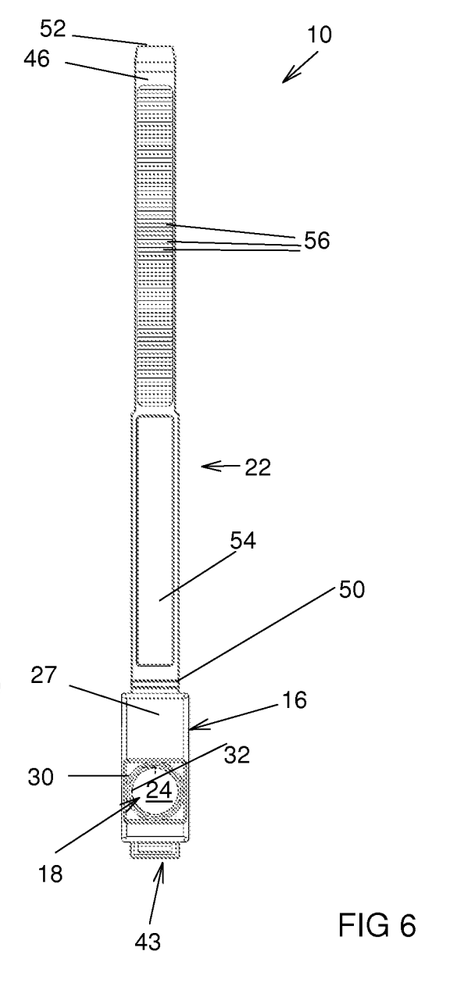
FIG. 6, in a top plan view, illustrates the styptic device shown in FIGS. 1 to 5 with the auxiliary compression element detached therefrom.

As seen in FIGS. 5 and 6, the base 16 includes a substantially parallelipiped shaped base main section 27 from which a substantially cylindrical main compression element support 28 protrudes. A substantially annular flange 30 extends substantially outwardly from the main compression element support 28 substantially away from the base main section 27 and defines a recess 32 for receiving, at least in part, the main compression element 18 thereinto.

The main compression element 18 is typically substantially resiliently deformable, and is made for example, of an hydrogenated copolymer of styrene, isoprene and butadiene. However, any other suitable materials are within the scope of the invention. It has been found that using a material having a Shore hardness of from about 15 A to about 50 A according to ASTM test D-2240 provided optimal results for the deformation properties of the main compression element. In a specific embodiment of the invention, the main compression element has a Shore hardness of about 30 A.

Typically, the main compression element 18 is substantially less rigid than the base 16. In some embodiments of the invention, the main compression element 18 has a shape, dimensions, and mechanical properties such that the main compression element 18 protrudes in the percutaneous puncture 12 when the main compression surface 24 is compressed against the patient 11 in register with the percutaneous puncture 12. This property is described in further details hereinbelow.

As seen in FIG. 5, in embodiments of the invention in which the main compression element 18 is received partially in the recess 32, the main compression element 18 defines a restrained portion 34 located in the recess 32 and an unrestrained portion 36 protruding from the recess 32. The restrained portion 34 is substantially prevented from deforming laterally in recess 32. The unrestrained portion 36 is substantially freely deformable to allow its partial insertion in the percutaneous puncture 12. By being substantially snuggly received in the recess 32, the restrained portion 34 helps in concentrating the deformations of the main compression element 18 in response to compressive forces substantially adjacent to the main compression surface 24, and therefore helps in the deformation of the main compression surface 24 into the percutaneous puncture 12.

The main compression element 18 is typically positioned such that the main compression surface 24 is located substantially opposed to the base 16 so that compressive forces can be easily exerted by the base 16 on the main compression element 18. To provides a substantially isotropic pressure on the percutaneous puncture 12, the main compression element 18 is typically substantially cylindrical. However, other shapes are within the scope of the present invention. Also, to facilitate positioning of the main compression element 18 relatively to the percutaneous puncture 12, the main compression element 18 is typically substantially transparent.

As seen for example in FIG. 1, the auxiliary compression element 20 is generally parallelepiped shaped and extends generally perpendicularly to the base main section 27. The auxiliary compression element 20 is provided with a substantially resiliently deformable material defining the auxiliary compression surface 26, which is typically made of a material similar to the material with which the main compression element 18 is manufactured.

In some embodiments of the invention, as shown in FIG. 1, the auxiliary compression element 20 defines an auxiliary compression element aperture 38 extending therethrough for receiving the main compression element 18 thereinto when the auxiliary compression element 20 is attached to the base 16. In these embodiments, both the main compression element 18 and the auxiliary compression element 20 contact the patient 11 when the styptic device 10 is in use. However, in alternative embodiments of the invention, no auxiliary compression element aperture 38 is provided and the auxiliary compression element 20 encloses the main compression element 18 when attached to the base 16.

Figure 2:
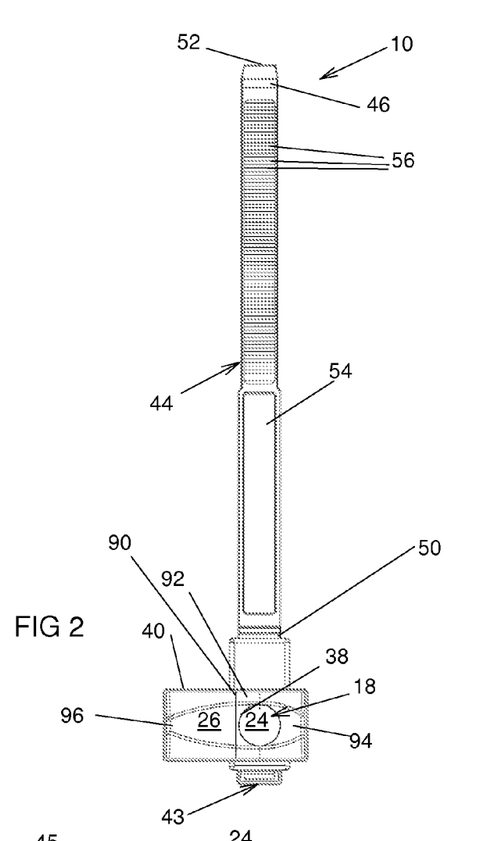
FIG. 2, in a top plan view, illustrates the styptic device shown in FIG. 1.

As seen for example in FIG. 2, the auxiliary compression element 20 is typically substantially elongated and defines a longitudinal midpoint 90. The auxiliary compression element aperture 38 is substantially longitudinally offset from the longitudinal midpoint 90. Typically, the auxiliary compression element 20 is attachable to the base 16 in a first orientation and in a second orientation, the longitudinal midpoint 90 being laterally located with respect to the base 16 on opposite sides of the base 16 when the auxiliary compression element 20 is attached to the base 16 in the first and second orientations. In the embodiment of the invention shown in the drawings, this is achieved by having a base 16 that presents a lateral and longitudinal symmetry about the main compression element 18. In these embodiments, attaching the auxiliary compression element 20 in the first and second positions allows for using the styptic device 10 in different orientations, for example for use on the left and right wrists of the patient 11.

The auxiliary compression surface 26 is also substantially elongated. By its shape, the auxiliary compression surface 26 creates an elongated pressure profile on the patient 11, which differs from a relatively symmetrical, or disc-shaped profile crated by the main compression surface 90. The auxiliary compression surface 26 defines a central section 92 and substantially longitudinally opposed end sections 94 and 96 extending from the central section 92. The end sections 94 and 96 taper in a direction leading substantially longitudinally away from the central section 92. This shape increases the pressure exerted by the auxiliary compression surface 26 on the patient 11 as a distance from the central section 92, which is typically substantially adjacent to the percutaneous puncture 12, increases. Since many blood vessels 14, such as the radial artery, are punctured at locations that are proximalmost to the skin surface of the patient 11, this configuration automatically provides a substantially uniform pressure on shallower and deeper sections of the blood vessel 14. This configuration helps in minimizing undesirable side effects of percutaneous punctures 12, such as those caused by hematomas.

The auxiliary compression element 20, when used, increases the surface area of the styptic device 10 that compresses the blood vessel 14, which improves the hemostatic properties of the styptic device 10 in relatively large patients 11. However, having the option of not using the auxiliary compression element 20 is useful in relatively small of thin patients 11.

Figure 4:
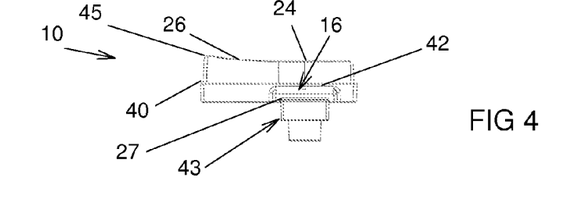
FIG. 4, in a front elevation view, illustrates the styptic device shown in FIGS. 1 to 3.

The auxiliary compression element 20 is typically hollow and defines a main compression element peripheral wall 40 extending substantially perpendicularly from the auxiliary compression surface 26. As better seen in FIG. 4, the main compression element peripheral wall 40 defines cut out portions 42 having a profile substantially similar to the transversal cross-section of the base main section 27 at the location at which the main compression element peripheral wall 40 engages the base main section 27.

Typically, the cut out portions 42 and the auxiliary compression element aperture 38 are dimensioned so that the auxiliary compression element 20 and the base 16 are attachable to each other in a press fit relationship relatively to each other. This specific method of attachment provides for relatively easy attachment and detachment of the base 16 and auxiliary compression element 20 to and from each other. However, other methods of attachment are also within the scope of the present invention.

The main and auxiliary compression surfaces 24 and 26 are typically substantially coplanar substantially adjacent to the main compression surface 24. Therefore, when the auxiliary compression element 20 is attached to the base 16, the main and auxiliary compression elements 16 and 20 define a compression surface it is substantially smooth and without discontinuity, as seen for example in FIG. 4.

In some embodiments of the invention, the auxiliary compression element 20 defines an auxiliary compression surface 26 that is substantially concave and which defines a nadir 47 substantially adjacent to the auxiliary compression element aperture 38 and a substantially spaced apart apex 45. This configuration is advantageous to produce pressure distribution profiles on the patient 11 that are non-uniform, as described in further details hereinbelow. However, in alternative embodiments of the invention, the auxiliary compression surface 26 is of any other suitable shape, such as a substantially flat shape, or a substantially convex shape, among other possibilities. It should be noted that in the drawings, the nadir 47 is relatively shallow as the curvature of the auxiliary compression surface 26 adjacent the nadir 47 is relatively small, but other curvatures are within the scope of the invention. Also, in some embodiments of the invention, the nadir 47 is not well-defined as the auxiliary compression surface 26 is substantially flat along a portion thereof.

Figure 3:
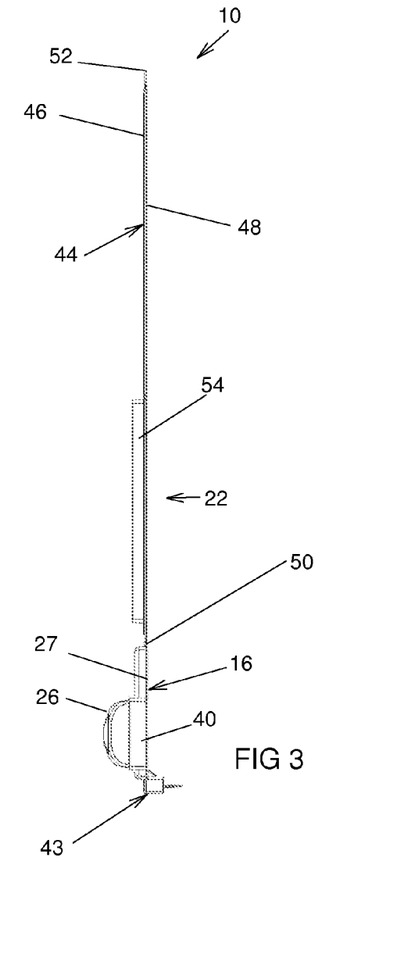
FIG. 3, in a side elevation view, illustrates the styptic device shown in FIGS. 1 and 2.

Referring for example to FIG. 3, the attachment 22 includes a substantially elongated strap 44 extending from the base main section 27. The strap 44 is typically made out of a substantially resilient polymer. The strap 44 defines a strap first side 46 and an opposed strap second side 48, the strap first side being provided on the same side of the styptic device 10 as the main compression element 18. Also, the strap 44 defines a strap first end 50 and a substantially longitudinally opposed strap second end 52. The strap 44 extends from the base main section 27 at the strap first end 50 and the strap second end 52 is a free end. The base main section 27 and the strap 44 are attached to each other, integrally molded together or mechanically secured to each other in any other suitable manner to the strap 44.

Typically, a cushion 54 is affixed onto the strap first side 46 at a location intermediate the strap first and second ends 50 and 52. The cushion 54 extends from a location substantially adjacent the base main section 27 toward the strap second end 52. The cushion 54 is typically made out of a relatively soft material, such as a gel. The cushion 54 helps in improving the comfort of the styptic device 10.

As seen in FIG. 2 for example, a series of substantially laterally extending grooves 56 extend substantially longitudinally spaced apart from each other along a portion of the strap 44. The grooves 56 are located between the cushion 54 and the strap second end 52. The grooves 56 extend into the strap first side 46 and are used to secure the strap 44 to the wrist of an intended user using a fastener 43.

Figure 7:
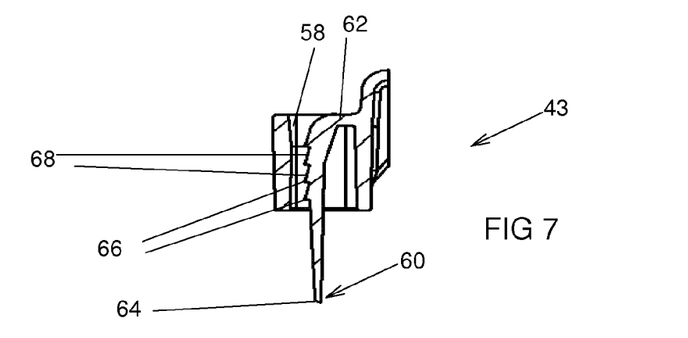

Referring for example to FIG. 7, the fastener 43 extends from the base 16 substantially opposed to the strap 44 and defines an aperture 58 extending substantially parallel to the recess 32. A tongue 60 is positioned inside the aperture 58 and defines a tongue first end 62 and a substantially longitudinally opposed tongue second end 64. The tongue first end 62 is secured to the base 16 so as to position the tongue 60 inside the aperture 58 substantially in the middle thereof. The tongue second end 64 is substantially freely movable such that the tongue 60 is sufficiently resiliently deformable to allow attachment of the strap 44 as described in further details hereinbelow. The tongue 60 defines substantially longitudinally spaced apart ledges 66, the ledges 66 being separated from each other by sloping surfaces 68. The ledges 66 are substantially parallel to the main compression surface 24 and the sloping surfaces 68 are such that the tongue 60 periodically becomes progressively increasingly thick in a direction leading from the strap first side 46 towards the strap second side 48.

the strap 44 and the fastener 43 are usable together to encircle a limb of the patient 11 to apply pressure with the styptic device 10. To that effect, the strap 44 is inserted into the aperture 58 to form a loop, with the strap first side 46 pointing inwardly. Tightening of the loop is relatively easy due to the slope of the sloping surfaces 68. However, loosening of the loop is relatively difficult due to the engagement of the ledges 66 with the grooves 56. To loosen the loop, the tongue 60 has to be deformed by pressing the tongue second end 64 toward the base 16, which disengages the ledges 66 and the grooves 56 from each other.

Figure 8:
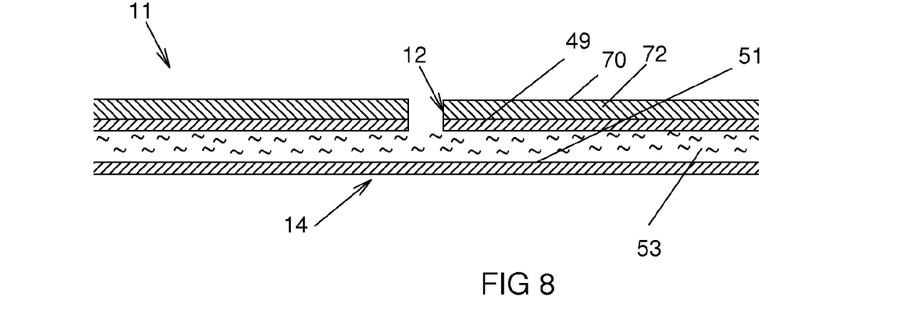
FIG. 8: in a side cross-sectional view, illustrates a percutaneous puncture.

As seen in FIG. 8, there is a need in some cases to stop blood flow from the percutaneous puncture 12. The percutaneous puncture 12 extends through an outer wall 49 of the blood vessel 14, the outer wall delimiting a lumen 51 in which blood 53 circulates. The percutaneous puncture 12 also extends through tissues extending between the skin surface 70 and the outer wall 49 to the blood vessel 14. For example, the tissue is skin tissue 72. However, in other embodiments of the invention, the blood vessel 14 is located deeper in the patient 11.

FIG. 9 illustrates a method in which the compression pressure is exerted with the main compression element 18 against the patient 11 substantially in register with the percutaneous puncture 12. In this method, a compression element, in this case the main compression element 18, deforms so that the main compression element 18 protrudes in the percutaneous puncture 12. In embodiments of the invention in which the percutaneous puncture 12 defines a puncture skin portion 74 extending through skin tissues 72, it is advantageous to deform the compression element 18 so that the compression element 18 protrudes in the percutaneous puncture 12 such that the puncture skin portion 74 is substantially entirely filled with the compression element 18. These embodiments allow for exerting relatively small pressures on the blood vessel 14 while preventing blood 53 from flowing out the blood vessels 14. This method is particularly advantageous as it reduces injuries to the blood vessel 14 and, therefore, facilitates healing of the patient 11. Typically, the compression pressure is decreased in steps after predetermined amounts of time until clotting has stopped bleeding completely, at which point the styptic device 10 can be removed.

In some embodiments of the invention, the auxiliary compression element 20 is used. The concave shape of the auxiliary compression element 20 creates a non-uniform pressure on the patient 11 along the auxiliary compression element 20. More specifically, when the apex 45 is positioned upstream of the percutaneous puncture 12, the pressure exerted upstream of the percutaneous puncture 12 may be larger than the compression pressure exerted at the percutaneous puncture 12. Since the upstream pressure exerted upstream of the percutaneous puncture 12 is larger than the compression pressure exerted at the percutaneous puncture 12, the blood vessel 14 may be obstructed by the upstream pressure, while allowing blood 53 from lateral vessels connected to the blood vessel 14 adjacent to the percutaneous puncture 12 to flow back towards the percutaneous puncture 12. This process conveys platelets to the percutaneous puncture 12, which helps in stopping blood flow relatively efficiently.

In alternative embodiments of the invention, the apex 45 is dimensioned so that the pressure exerted on the targeted blood vessel 16 is substantially uniform along the auxiliary compression component 20 and, as such, compensates for pressure diffusion caused by thickening of the tissue extending between the skin surface 50 and the blood vessel 16 at different locations along the blood vessel 16.

Although the present invention has been described hereinabove by way of preferred embodiments thereof, it can be modified, without departing from the spirit and nature of the subject invention as defined in the appended claims.

What is claimed is:

1. A styptic device for substantially hemostatically sealing a percutaneous puncture in a blood vessel of a patient, said styptic device comprising:
   a base;
   a main compression element extending from said base, said main compression element defining a main compression surface compressible against said patient; and
   an auxiliary compression element removably attachable to said base, said auxiliary compression element defining an auxiliary compression surface compressible against said patient, said main and auxiliary compression surfaces being exposed and compressible against said patient when said auxiliary compression element is attached to said base;

wherein said auxiliary compression element defines an auxiliary compression element aperture extending therethrough for receiving said main compression element when said auxiliary compression element is attached to said base; and wherein, when compressed on said patient substantially in register with said percutaneous puncture, said styptic device exerts a first pressure distribution profile on said patient substantially adjacent to said percutaneous puncture when said auxiliary compression element is attached to said base and said styptic device exerts a second pressure distribution profile on said patient substantially adjacent to said percutaneous puncture when said auxiliary compression element is detached from said base, said first and second pressure distribution profiles being different from each other.

2. A styptic device as defined in claim 1, wherein said main compression element is substantially resiliently deformable.

3. A styptic device as defined in claim 2, wherein said main compression element is substantially less rigid than said base.

4. A styptic device as defined in claim 2, wherein said main compression element has a shape, dimensions and mechanical properties such that said main compression element protrudes in said percutaneous puncture when said main compression surface is compressed against said patient in register with said percutaneous puncture.

5. A styptic device as defined in claim 2, wherein said base defines a recess for receiving, at least in part, said main compression element thereinto.

6. A styptic device as defined in claim 5, wherein said main compression element defines a restrained portion located in said recess and an unrestrained portion protruding from said recess.

7. A styptic device as defined in claim 1, wherein said auxiliary compression element is provided with a substantially resiliently deformable material defining said auxiliary compression surface.

8. A styptic device as defined in claim 1, wherein said main and auxiliary compression surfaces are substantially coplanar substantially adjacent to said main compression surface.

9. A styptic device as defined in claim 8, wherein said auxiliary compression surface is substantially concave and defines a nadir substantially adjacent to said auxiliary compression element aperture.

10. A styptic device as defined in claim 1, wherein said auxiliary compression element is substantially elongated and defines a longitudinal midpoint, said auxiliary compression element aperture being substantially longitudinally offset from said longitudinal midpoint.

11. A styptic device as defined in claim 10, wherein said auxiliary compression element is attachable to said base in a first orientation and in a second orientation, said longitudinal midpoint being laterally located with respect to said base on opposite sides of said base when said auxiliary compression element is attached to said base in said first and second orientations.

12. A styptic device as defined in claim 1, wherein said auxiliary compression surface is substantially concave.

13. A styptic device as defined in claim 1, wherein said auxiliary compression element and said base are attachable to each other in a press fit relationship relatively to each other.

14. A styptic device as defined in claim 1, further comprising an attachment operatively coupled to said base for attaching said styptic device to said patient.

15. A styptic device as defined in claim 14, wherein said attachment includes a strap for encircling a limb of said patient.

16. A styptic device as defined in claim 1, wherein said main compression surface is substantially opposed to said base relatively to said main compression element.

17. A styptic device as defined in claim 1, wherein said main compression element is substantially transparent.

18. A styptic device as defined in claim 1, wherein said main compression element is substantially cylindrical.

19. A styptic device as defined in claim 1, wherein said auxiliary compression surface is substantially elongated.

20. A styptic device as defines in claim 19, wherein said auxiliary compression surface defines a central section and substantially longitudinally opposed end sections extending from said central section, said end sections tapering in a direction leading substantially longitudinally away from said central section.

21. A styptic device as defined in claim 1, wherein said main compression element extends integrally from said base.

* * * * *